United States Patent [19]

Costa

[11] 4,316,045

[45] Feb. 16, 1982

[54] CATALYTIC PROCESS FOR THE PRODUCTION OF ARYL CARBOXYLATES

[75] Inventor: Lawrence C. Costa, Nanuet, N.Y.

[73] Assignee: The Halcon SD Group, Inc., New York, N.Y.

[21] Appl. No.: 182,512

[22] Filed: Aug. 29, 1980

[51] Int. Cl.$^3$ .............................................. C07C 67/00
[52] U.S. Cl. .............................. 560/130; 260/345.8 R; 260/346.22; 260/347.4; 260/465 R; 549/52; 560/51; 560/53; 560/54; 560/84; 560/96; 560/105; 560/129; 560/139; 560/141; 560/142; 560/143; 560/144; 560/146
[58] Field of Search ............... 560/105, 139, 142, 143, 560/144, 146, 96, 84, 51, 53, 54, 129, 141, 130; 549/52; 260/410.5, 345.8 R, 347.4, 346.22, 465 R

[56] References Cited

U.S. PATENT DOCUMENTS

| 3,574,777 | 4/1971 | Heck | 560/53 |
| 3,700,727 | 10/1972 | Heck | 260/347.4 |
| 3,705,919 | 12/1972 | Heck | 560/54 |
| 3,917,670 | 11/1975 | Baird, Jr. et al. | 260/347.4 |
| 4,182,915 | 1/1980 | Harvey | 568/716 |

FOREIGN PATENT DOCUMENTS 47-10705  3/1972  Japan ..................................... 560/96

*Primary Examiner*—Natalie Trousof
*Assistant Examiner*—Frederick W. Pepper
*Attorney, Agent, or Firm*—William C. Long; David Dick; Riggs T. Stewart

[57] ABSTRACT

A process for the catalytic preparation of aryl carboxylates is provided in which an arylmetallo carboxylate is contacted in liquid medium with an organic peracid in the presence of a catalytic amount of an aryl iodide, to form the desired aryl carboxylate.

7 Claims, No Drawings

CATALYTIC PROCESS FOR THE PRODUCTION OF ARYL CARBOXYLATES

CROSS-REFERENCE TO RELATED APPLICATION

This application is related to my co-pending application entitled "Process for the Preparation of Aryl Carboxylates", Ser. No. 182,529, filed Aug. 29, 1980.

BACKGROUND OF THE INVENTION

1. Field of the Invention

This invention relates to the preparation of aryl carboxylates and more particularly to the catalytic production of aryl carboxylates by reaction of arylmetallo carboxylates with organic peracids in the presence of an aryl iodide catalyst.

2. Description of the Prior Art

Aryl carboxylates, such as phenyl carboxylates (e.g., phenyl acetate, phenyl salicylate and the like) find a wide variety of uses. For example, phenyl acetate can be hydrolyzed to prepare phenol, and also finds use as a solvent. Phenyl salicylate is used as a preservative.

Various methods for preparing aryl carboxylates are known. For example, phenyl acetate can be prepared from the reaction of phenol and acetyl chloride or acetic anhydride, or by heating triphenyl phosphine in the presence of potassium acetate and alcohol. See, e.g., *Condensed Chemical Dictionary*, 8th Ed., p. 678 (1971). Also known is a process for preparing aryl carboxylates by reaction of aryl thallium (III) metallates with the corresponding carboxylic acid. See U.S. Pat. No. 4,182,915 (issued in 1980 to R. J. Harvey).

Diaryl mercury compounds are known to react with aryl iodoso dihalides to produce a diaryliodonium halide and an aryl mercuric halide compound. F. M. Beringer, et al., 75 *J. Amer. Chem. Soc.* 2705 (1953). Also known is the reaction of phenyl magnesium chloride with phenyl iodoso dichloride to produce a complex mixture of products which has been variously reported as being only phenyl iodide and diphenyl or a mixture of phenyl chloride, phenyl iodide, diphenyl and diphenyl iodonium chloride. R. B. Sandix, 32 *Chem. Rev.* 249, at 261 (1943).

The use of such diaryl iodonium salts in various synthesis reactions has been reported in a number of references. In addition to the above two articles by Beringer, et al. and Sandix, illustrative literature on this subject includes F. M. Beringer, et al., 75 *J. Amer. Chem. Soc.* 2708 (1953); M. C. Caserio, et al., 81 *J. Amer. Chem. Soc.* 336 (1959); F. M. Beringer, et al., 81 *J. Amer. Chem. Soc.* 342 (1959); and F. M. Beringer, et al., 81 *J. Amer. Chem. Soc.* 351 (1959). Studies of use of diphenyl iodonium salts in hydrolysis reactions show copper (I) and copper (II) to be catalysts for the hydrolysis reaction. The non-catalyzed hydrolysis reaction is suppressed by the presence of acid. The copper catalyzed reaction was also found, in varying degrees, to be retarded by the presence of acid.

Diphenyliodonium bromide has been reacted with sodium benzoate to form phenyl benzoate and phenyl iodide, and the reaction has been found to be faster in strong bases. F. M. Beringer, et al., 75 *J. Amer. Chem. Soc.* 2708 (1963).

SUMMARY OF THE INVENTION

According to the process of this invention, arylmetallo carboxylates are reacted in liquid medium with an organic peracid in the presence of a catalytic amount of an aryl iodide.

DETAILED DESCRIPTION OF THE INVENTION

The arylmetallo carboxylates which are useful as reactants in the process of this invention comprise compounds having the formula:

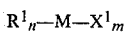

$$R^1{}_n-M-X^1{}_m$$

wherein $R^1$ is a mono- or polynuclear aryl; M is a metal cation selected from the group consisting of Hg, Sn, Tl, Pb and Cd; $X^1$ is a carboxylate group of from 2 to 20 carbon atoms derived from an aliphatic or aromatic mono- or di- carboxylic acid; and n and m are each integers of from 1 to (t−1), wherein t is the valence of the M metal cation, with the proviso that n+m=t.

The metal cations "M" of the foregoing arylmetallo carboxylate reactants will be in their highest respective normal oxidation state. Thus, the valences of the metal cations in the reactants will be as follows: $Hg^{2+}$, $Sn^{4+}$, $Tl^{3+}$, $Pb^{4+}$ and $Cd^{2+}$. Compounds containing any of the foregoing metals in lower valences can be present in the reaction zone and do not interfere with the desired reaction.

The $R^1$ aryl group can be substituted or unsubstituted; and will generally each have a total of from about 6 to 18 carbon atoms, and preferably from about 6 to 14 carbon atoms. When substituted, suitable organic substituents include alkyl of 1 to 12 carbon atoms, cycloalkyl of 4 to 12 carbon atoms, heterocyclic having from 6 to 10 member rings containing one or more O or S ring atom, cyano, keto having from 2 to 10 carbon atoms, and carboalkoxy having from 2 to 10 carbon atoms. Illustrative of the foregoing organic substituents are methyl, butyl, decyl, cyclobutyl, cyclooctyl, cyclododecyl, furyl, pyranyl, benzofuranyl, benzothiofuranyl, cyano, acetyl, butanoyl, benzoyl, carbomethoxy, carboheptoxy and the like. Suitable inorganic substituents to the $R^1$ group include halide (e.g., Cl, F, I and Br), nitro, hydroxy, sulfo and the like.

Illustrative of suitable $R^1$ aryl groups are phenyl, 2-tolyl, 2,4-xylyl, 3-cyclohexyl phenyl, 4-tolyl, 2-isopropylphenyl, 3-isopropylphenyl, 4-isopropylphenyl, 2-carboxylphenyl, 2-hydroxyphenyl, 2-cyanophenyl, 3-nitrophenyl, 2,3-dichlorophenyl, naphthyl, and the like. Preferred as the $R^1$ aryl groups in the practice of this invention are phenyl, 2-, 3-, and 4-isopropylphenyl, and naphthyl, with phenyl being especially preferred.

Exemplary aliphatic monocarboxylic acids from which such $X^1$ carboxylate moieties can be derived are branched and straight-chained acids such as acetic, propionic, isobutyric, pentanoic, hexanoic, octanoic, decanoic, and the like, and aryl-substituted derivatives of the foregoing such as phenylacetic acid and the like. Exemplary aliphatic dicarboxylic acids are oxalic, malonic, succinic, glutaric, adipic and the like. Exemplary aromatic carboxylic acids are terephthalic, isophthalic, phthalic and the like.

The foregoing aliphatic and aromatic mono- and di-carboxylic acids can be substituted or unsubstituted, and when substituted can contain such substituents as hydroxy, cyano, keto, carboalkoxy, nitro, halo (e.g., fluoro, chloro and bromo), and the like. Exemplary of such substituted acids, from which the $X^1$ moieties can be derived, are salicylic acid, m-chlorobenzoic acid, 4-hydroxybenzoic acid, trifluoroacetic acid and the like.

Therefore, illustrative of suitable arylmetallo carboxylate reactants of this invention are phenylmercuric acetate, triphenyl tin acetate, tolylmercuric acetate, tolyltin triacetate, 4-isopropylphenylthallium diacetate, phenylthallium ditrifluoroacetate, and the like.

Organic peracids useful in the process of this invention are organic compounds containing one or more

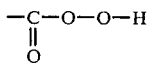

moiety per molecule and therefore include peracids of the formula (II):

wherein $R^2$ is H, alkyl of from 1 to 20 carbon atoms, aryl of from 6 to 14 carbon atoms, alkaryl or aralkyl of from 7 to 20 carbon atoms, cycloalkyl of from 3 to 12 carbon atoms, and halogenated derivatives of the foregoing groups. Illustrative of suitable peracids, therefore, are peracetic, perpropionic, perbenzoic, pertrifluoroacetic, m-chloroperbenzoic, performic, and the like. Preferred organic peracids are peracids of the above formula (II) wherein the $R^2$ group is alkyl of from 1 to 6 carbon atoms and halogenated derivatives thereof. Illustrative of such preferred peracids are peracetic acid, performic acid, pertrifluoroacetic acid and the like.

The aryl iodide catalysts of this invention comprise at least one compound of the formula (III):

wherein $R^3$ is mono- or polynuclear aryl having a total of from 6 to 18 carbon atoms, and preferably from 6 to 14 carbon atoms. The $R^3$ group can be substituted or unsubstituted, and when substituted can contain such substituents as alkyl of 1 to 12 carbon atoms, cycloalkyl of 4 to 12 carbon atoms, heterocyclic having from 6 to 10 member rings containing one or more ring S or O atom, cyano, keto having from 2 to 10 carbon atoms, carboalkoxy of from 2 to 10 carbon atoms, alkoxy of from 1 to 10 carbon atoms, carboxylate of from 1 to 10 carbon atoms, halide (e.g., Cl, F, I and Br), nitro, hydroxy, sulfo and the like).

Especially preferred aryl iodide catalysts in this invention are phenyl iodide, and its lower alkyl-substituted derivatives, such as tolyl iodide, isopropylphenyl iodide, ethylphenyl iodide and the like.

The foregoing reactants and catalyst are contacted in accordance with this invention in liquid medium. The conditions of temperature and pressure which are employed in the reaction are not critical and may vary widely. Generally, temperatures of from about 25° to 150° C. will be entirely sufficient, with temperatures from about 50° to 100° C. being more usually employed.

Pressure is not a critical parameter of the process of this invention and the reaction can be run at any convenient pressure, including atmospheric, subatmospheric or superatmospheric pressure. An inert atmosphere is not required and therefore the reaction can be conveniently operated in the presence of air.

The arylmetallo carboxylate and organic peracid reactants of this invention are preferably contacted in a molar ratio of from about 10:1 to 1:10, more preferably from about 1:1 to 1:3. However, these ratios are not critical, it being recognized that use of the organic peracid in an amount less than that which is stoichiometrically required to react with the quantity of aryl metallo carboxylate present in the reaction medium will only limit the yield of aryl carboxylate, based on aryl metallo carboxylate charged.

The aryl iodide catalyst of this invention will be generally employed in the reaction zone in an amount of from about 1 to 50 wt. %, preferably from about 5 to 40 wt. %, and more preferably from about 10 to 20 wt. %, based on the amount of the arylmetallo carboxylate charged.

The reaction is preferably conducted in the substantial absence of strong organic bases, such as pyridine, since these compounds have been found to severely inhibit the formation of the desired aryl carboxylates. For the purpose of this invention, the term "strong organic base" is intended to mean organic compounds which have a base association constant $(K_b)$ such that the $pK_b$ (where $pK_b = -\log K_b$) is not greater than $-3.5$, wherein "$K_b$" is determined by the equilibrium:

$$Base + H^+ \rightleftharpoons Base \cdot H^+$$

and is defined by the expression:

$$K_b = \frac{[Base \cdot H^+]}{[Base][H^+]}$$

in which [Base], [Base.H+] and [H+] are the concentrations, in mole/liter, of the basic compound, its associated conjugate acid and H+ ion, respectively, at 25° C.

The reaction time may vary widely, but the reaction will generally be complete after a period of 0.1 to 20 hours, and preferably from 1 to 6 hours.

The reaction in accordance with the process of this invention is employed in liquid medium. Suitable solvents include alcohols (e.g., lower alkanols such as methanol, ethanol, tertbutanol, and the like), ethers (e.g., tetrahydrofuran, dioxane and the like), nitriles (e.g., acetonitrile, benzonitrile, iosbutyronitrile and the like), ketones (e.g., acetone, methyl ethyl ketone, acetophenone and the like), amides (e.g., dimethyl formamide, dimethylacetamide, N-methyl-pyrrolidione, and the like), esters (e.g., esters of lower monocarboxylic acids, such as ethylene glycol diacetate, propylene glycol diacetate, and the like), and carboxylic acids (e.g., any of the carboxylic acids discussed above). Mixtures of organic solvents and water are also suitable. Carboxylic acids, either alone or in combination with water, are especially preferred as liquid medium for this reaction.

The process of this invention can be performed in a batchwise semi-continuous manner, and the manner of contacting the reactants is not critical. Thus, the arylmetallo carboxylate, organic peracid, aryl iodide catalyst and solvent can be pre-mixed or fed separately to the reaction vessel.

The effluent from the reaction vessel can be treated by conventional means to recover the desired aryl carboxylate product therefrom. Aryl iodide catalyst can also be recovered and recycled to the process.

Alternatively, after removal of the aryl iodide catalyst and metallo acetate by-products, the aryl carboxylate can then be contacted with water or another source of a hydroxy group to form the corresponding phenol from the aryl carboxylate. Thus phenyl acetate can be contacted with water to form phenol.

The process of this invention can be further illustrated by reference to the following examples, wherein parts are by weight unless otherwise indicated.

EXAMPLE 1

To a round bottom glass flask is added 5 mmols of phenyl mercuric acetate, 5 mmols of phenyl iodide, 10 mmols of peracetic acid and 10 ml. of acetic acid as solvent. The resulting liquid mixture is stirred employing a magnetic stirrer and heated by means of an oil bath to a temperature of about 75° C. for a period of about 4 hours. The flask is open to the atmosphere during the experiment. At the end of the 4 hours of reaction, the liquid mixture in the flask is analyzed by gas chromotography. Phenyl mercuric acetate conversion is found to be about 62%, and phenyl acetate is found to be produced in a selectivity of about 74%, and in a yield of about 46%, based on phenyl mercuric acetate charged.

EXAMPLE 2

Following the procedure of Example 1, 5 mmols of phenyl mercuric acetate, 5 mmols of peracetic acid and 1.0 mmol of phenyl iodide, together with 20 ml. of acetic acid as solvent, are charged to the reaction vessel. After 18 hours of reaction at a temperature of 75° C., phenyl acetate yield is found to be formed in a yield of about 10%, based on the phenyl mercuric acetate charged. Analysis of the liquid product mixture shows it to contain 1 mmol of phenyl iodide, thereby demonstrating the catalytic effect of phenyl iodide upon the reaction.

EXAMPLE 3 FOR COMPARISON

The procedure of Example 2 is repeated in a series of runs. In the first run, the charge to the reaction vessel consists only of the phenyl mercuric acetate, peracetic acid and acetic acid solvent. No phenyl iodide is employed. At the end of the reaction time, the liquid mixture is found to contain no detectable phenyl acetate.

In the second run, the charge to the reaction vessel consists of the phenyl mercuric acetate, phenyl iodide and acetic acid solvent. In this run, no peracetic acid is employed. Again, after the reaction time has elapsed, the liquid mixture is found to contain no detectable amount of phenyl acetate.

These runs illustrate the criticality of use of both an organic peracid and an aryl iodide of this invention.

EXAMPLE 4 FOR COMPARISON

The procedure of Example 1 is repeated except that 5 mmols of benzene are employed instead of the phenyl iodide of Example 1. Also, an additional 10 mls. of acetic acid solvent is employed. After the 4 hours of reaction at 75° C., no detectable phenyl acetate is formed. This again underscores the criticality of use of an aryl iodide of this invention as catalyst.

EXAMPLE 5

The procedure of Example 1 is repeated except that 5 mmols of triphenyl tin acetate are employed instead of the phenyl mercuric acetate of Example 1, and 30 mmols of peracetic acid is used. After 4 hours of reaction at 75° C. there is obtained phenyl acetate in a yield of about 58%, and in a selectivity of about 68%, at a triphenyl tin acetate conversion of about 85%.

It will be obvious that various changes and modifications may be made without departing from the invention and it is intended, therefore, that all matter contained in the foregoing description shall be interpreted as illustrative only and not limitative of the invention.

I claim:

1. A process for preparing an aryl carboxylate which comprises contacting (a) an arylmetallo carboxylate of the formula:

$$R^1_n-M-X^1_m$$

wherein $R^1$ is a mono- or polynuclear substituted or unsubstituted aryl group having a total of from 6 to 18 carbon atoms; M is a metal cation in its highest oxidation state selected from the group consisting of Hg, Sn, Tl, Pb and Cd cations; $X^1$ is a carboxylate group of from 2 to 20 carbon atoms derived from an aliphatic or aromatic mono- or di- carboxylic acid; and n and m are each integers of from 1 to (t−1), wherein t is the valence of the M metal cation, with the proviso that n+m=t, with (b) an organic peracid of the formula:

$$R^2-\underset{\underset{O}{\|}}{C}-O-O-H$$

wherein $R^2$ is H, alkyl of from 1 to 20 carbon atoms, aryl of from 6 to 14 carbon atoms, alkaryl or aralkyl of from 7 to 20 carbon atoms, cycloalkyl of from 3 to 12 carbon atoms, and halogenated derivatives of the foregoing groups, in liquid medium in the presence of a catalytic amount of an aryl iodide of the formula:

$$R^3-I$$

wherein $R^3$ is mono- or polynuclear aryl having a total of from 6 to 18 carbon atoms to form the corresponding aryl carboxylate.

2. The process according to claim 1 wherein the liquid medium is maintained at a temperature of from about 25° to 150° C.

3. The process according to claim 1 wherein the aryl iodide catalyst is employed in an amount of from about 1 to 50 wt. %, based on the amount of the arylmetallo carboxylate charged.

4. The process according to claim 1 wherein the reaction is conducted in the substantial absence of a strong organic base.

5. The process according to claim 1 wherein the $R^1$ aryl moiety of said arylmetallo carboxylate comprises phenyl, naphthyl, 2-, 3-, or 4-isopropyl phenyl, and wherein the carboxylate $X^1$ moiety of said arylmetallo carboxylate is derived from an aliphatic saturated monocarboxylic acid having from 1 to 6 carbon atoms.

6. The process according to claim 1 wherein the organic peracid comprises a member selected from the group consisting of alkyl peracids having from 1 to 6 carbon atoms and halogenated derivatives thereof.

7. The process according to claim 1 wherein the arylmetallo carboxylate and organic peracid are employed in the liquid medium and a molar ratio of from about 10:1 to 1:10.

* * * * *